(12) United States Patent
Brown

(10) Patent No.: US 11,376,044 B2
(45) Date of Patent: Jul. 5, 2022

(54) SYSTEMS AND METHODS USING MICRO-ELECTROMAGNETS SECURED TO BONE STRUCTURE FOR STABILIZATION, FIXATION, AND ACCELERATED HEALING

(71) Applicant: Set Point Solutions, LLC, Tampa, FL (US)

(72) Inventor: Joseph Harrington Matanane Brown, Toto, GU (US)

(73) Assignee: Set Point Solutions, LLC, Tampa, FL (US)

( * ) Notice: Subject to any disclaimer, the term of this patent is extended or adjusted under 35 U.S.C. 154(b) by 5 days.

(21) Appl. No.: 16/805,615

(22) Filed: Feb. 28, 2020

(65) Prior Publication Data

US 2021/0267641 A1 Sep. 2, 2021

(51) Int. Cl.
| | | |
|---|---|---|
| A61B 17/68 | (2006.01) | |
| A61B 17/70 | (2006.01) | |
| A61B 17/00 | (2006.01) | |
| A61B 17/56 | (2006.01) | |

(52) U.S. Cl.
CPC ............ *A61B 17/68* (2013.01); *A61B 17/70* (2013.01); *A61B 2017/00212* (2013.01); *A61B 2017/00221* (2013.01); *A61B 2017/00876* (2013.01); *A61B 2017/564* (2013.01); *A61B 2017/681* (2013.01)

(58) Field of Classification Search
CPC ......... A61B 17/70; A61B 17/68; A61B 17/80; A61B 17/72; A61N 1/36; A61F 2/28; A61L 31/122
See application file for complete search history.

(56) References Cited

U.S. PATENT DOCUMENTS

| | | | | |
|---|---|---|---|---|
| 4,315,503 A | * | 2/1982 | Ryaby ...................... | A61N 2/02 600/14 |
| 7,029,431 B2 | * | 4/2006 | Apple .................... | A61B 17/68 600/3 |
| 7,060,075 B2 | * | 6/2006 | Govari ............... | A61B 17/1707 606/98 |
| 8,057,472 B2 | * | 11/2011 | Walker ................... | A61B 17/68 606/57 |
| 8,277,506 B2 | * | 10/2012 | Krueger ............. | A61B 17/8805 623/17.12 |

(Continued)

*Primary Examiner* — Christopher J Beccia
(74) *Attorney, Agent, or Firm* — Middleton Reutlinger; Alexander P. Brackett

(57) ABSTRACT

Embodiments of the present technology pertain to a system for hyper-localized immobilization of a bone structures. In various embodiments the system includes a power supply, the power supply being internal or external to a patient and allowing for variable control of electric current from the power supply. Embodiments further include a first micro-electromagnet being internal to the patient and being placed in a first bracket that is secured to a first side of the bone structure generating half of an electromagnetic attractive force that will immobilize the other bone structure when a second micro-electromagnet being internal to the patient is placed in a second bracket that is secured to a second side of the bone structure generating the electromagnetic attractive force that immobilizes the bone structure. This method could be applied to stabilize or fixate bone fracture sites when electromagnets leverage attractive forces.

20 Claims, 5 Drawing Sheets

(56) References Cited

U.S. PATENT DOCUMENTS

| | | | | |
|---|---|---|---|---|
| 8,301,262 B2* | 10/2012 | Mi | ............... | A61B 5/0031 |
| | | | | 607/60 |
| 8,496,657 B2* | 7/2013 | Bonutti | ............ | A61B 17/0401 |
| | | | | 606/62 |
| 8,715,282 B2* | 5/2014 | Pool | ............... | A61B 17/7216 |
| | | | | 606/62 |
| 9,526,441 B2* | 12/2016 | Wilhelm | ............ | A61B 17/72 |
| 9,987,140 B2* | 6/2018 | Ling | ............ | A61B 17/7016 |
| 10,307,588 B2* | 6/2019 | Tacktill | ............ | A61N 1/326 |
| 2008/0255560 A1* | 10/2008 | Myers | ............ | A61B 17/7225 |
| | | | | 606/63 |
| 2010/0289491 A1* | 11/2010 | Budker | ............ | G01R 33/26 |
| | | | | 324/304 |

\* cited by examiner

SYSTEMS AND METHODS USING MICRO-ELECTROMAGNETS SECURED TO BONE STRUCTURE FOR STABILIZATION, FIXATION, AND ACCELERATED HEALING

FIELD OF THE INVENTION

The present technology relates generally to medical devices. More particularly, but not by limitation, to using devices using micro-electromagnets secured to bone structure for anatomical structure stabilization, fixation, and accelerated healing.

BACKGROUND OF THE DISCLOSURE

Sustaining fractures to bone structure is a common injury. When these injuries impact specific bone structures, however, the impact can be extensive, and the remedy can be particularly challenging. For example, bilateral fractures of pars interarticularis may result in anterolisthesis and spondylolisthesis. In other words, the bones that hold vertebrae in place may completely crack off allowing the vertebra to shift and pinch the spinal cord causing severe pain for a patient.

One problem is that the current state of the art is to mechanically set and then immobilize an injury site (e.g., a spinal injury site such as an L5-S1 vertebra joint facture) using hardware. Example hardware for immobilization of the injury site may be external fixators (rods, pins, bolts, etc.), plates, brackets, and/or external casts. Immobilization of the injury site using hardware unfailingly leads to atrophy of the surrounding muscle tissue. Furthermore, using hardware (e.g., rods, pins, bolts, plates, brackets, etc.) potentially causes unnecessary trauma to the tissues surrounding the injury site, resulting in increased healing times, and oftentimes permanent or semi-permanent placement of the hardware at the injury site that permanently limits range of motion for a patient and may prevent a patient from recovering and being physically able to enjoy their hobbies or perform their profession. Thus, there is a need to immobilize an injury site without using extensive hardware.

SUMMARY

The present disclosure may be directed to a system for hyper-localized immobilization of a bone fracture injury site using micro-electromagnets secured to fractured bone of the bone fracture injury site causing accelerated healing. In some embodiments the system comprises: (A) a power supply, the power supply potentially being external to a patient and allowing control of electric current from the power supply; (B) a first micro-electromagnet being internal to the patient and being placed within a bracket that is secured to a first side of the fractured bone of the bone fracture injury site, the first micro-electromagnet being electronically connected to a positive lead connected to the power supply, the positive lead receiving the electric current from the power supply generating half of an electromagnetic attractive force that will immobilize the fractured bone of the bone fracture injury site; and (C) a second micro-electromagnet being internal to the patient and being placed within a bracket that is secured to a second side of the fractured bone of the bone fracture injury site, the second micro-electromagnet being electrically connected to a negative lead connected to the power supply, the negative lead receiving the electric current from the power supply generating the other half of the electromagnetic attractive force that will immobilize the fractured bone of the bone fracture injury site.

In various embodiments the first micro-electromagnet is secured within a bracket that is itself secured to the first side of the fractured bone of the bone fracture injury site using epoxy and bone meal; and the second micro-electromagnet is secured within a bracket that is itself secured to the second side of the fractured bone of the bone fracture injury site using epoxy and bone meal.

In some embodiments the interior of the fracture site can be mechanically scored with corresponding male and female segments to form a joint—this scoring further traumatizes the bone structure in an effort to induce a more aggressive healing response. The healing response may be further aided with the use of stem cell treatment and the resultant exposure to the device's emitted electromagnetic fields.

In various embodiments the first micro-electromagnet is secured within a bracket that is itself secured to the first side of the fractured bone of the bone fracture injury site using dental resin cured using ultraviolet light; and the second micro-electromagnet is secured within a bracket that is itself secured to the second side of the fractured bone of the bone fracture injury site using dental resin cured using ultraviolet light.

In some embodiments the power supply being external to the patient provides variable electric current greater than a baseline electric current, the increased electric current causing increased pressure of the bone fracture injury site compared with a baseline pressure that enhances immobilization of the fractured bone of the bone fracture injury site allowing for personalized healing of the bone fracture injury site.

In various embodiments the power supply provides variable electric current less than a baseline electric current, the decreased electric current causing decreased pressure of the bone fracture injury site compared with a baseline pressure that diminishes immobilization of the fractured bone of the bone fracture injury site allowing for personalized healing of the bone fracture injury site.

In some embodiments the first micro-electromagnet secured within a bracket that is itself secured to the first side of the fractured bone of the bone fracture injury site is square shaped; and the second micro-electromagnet secured within a bracket that is itself secured to the second side of the fractured bone of the bone fracture injury site is square shaped.

In some embodiments a first plurality of micro-electromagnets being internal to the patient and being secured within a bracket that is itself secured to the first side of the fractured bone of the bone fracture injury site, the first plurality of micro-electromagnets enhancing electromagnetic fields of the first micro-electromagnet; and a second plurality of micro-electromagnets being internal to the patient and being secured within a bracket that is itself secured to the second side of the fractured bone of the bone fracture injury site, the second plurality of micro-electromagnets enhancing electromagnetic fields of the second micro-electromagnet.

The present disclosure may be directed to a method for hyper-localized immobilization of a bone fracture injury site using micro-electromagnets secured to fractured bone of the bone fracture injury site causing accelerated healing. In various embodiment the method comprises: (I) supplying power from a power supply, the power supply may be external to a patient and allowing for patient control of electric current from the power supply or the power supply may be internal and collocated with the electromagnet, with output amperage only able to be controlled remotely by the medical professional via Bluetooth or similar technology; (II) receiving the electric current from the power supply at a first micro-electromagnet internal to the patient, the first micro-electromagnet being secured within a bracket that is itself secured to a first side of the fractured bone of the bone fracture injury site, and the first micro-electromagnet being electronically connected to a positive lead connected to the power supply, the positive lead receiving the electric current from the power supply causing half of an electromagnetic attractive force that immobilize the fractured bone of the bone fracture injury site; and (III) receiving the electric current from the power supply at a second micro-electromagnet internal to the patient, the second micro-electromagnet being secured within a bracket that is itself secured to a second side of the fractured bone of the bone fracture injury site, and the second micro-electromagnet being electrically connected to a negative lead connected to the power supply, the negative lead receiving the electric current from the power supply causing the other half of the electromagnetic attractive force that will immobilize the fractured bone of the bone fracture injury site.

The present disclosure may be directed to a method for hyper-localized immobilization of a bone migration site using micro-electromagnets secured to opposing sides of bones migrating beyond where they anatomically should reside (i.e. due to vertebral disc compression, disc desiccation, tendon necrosis, deterioration of cartilage, etc.). In various embodiments the method comprises: (I) supplying power from a power supply, the power supply may be external to a patient and allowing for patient control of electric current from the power supply or the power supply may be internal and collocated with the electromagnet, with output amperage only able to be controlled remotely by the medical professional via Bluetooth or similar technology; (II) receiving the electric current from the power supply at a first micro-electromagnet internal to the patient, the first micro-electromagnet being secured within a bracket that is itself secured to a first side of the bone migration site, and the first micro-electromagnet being electronically connected to a negative lead connected to the power supply, the negative lead receiving the electric current from the power supply causing half of an electromagnetic repulsive force that will immobilize the bone migration site; and (III) receiving the electric current from the power supply at a second micro-electromagnet internal to the patient, the second micro-electromagnet being secured within a bracket that is itself secured to a second side of the bone migration site, and the second micro-electromagnet being electrically connected to a negative lead connected to the power supply, the negative lead receiving the electric current from the power supply causing the other half of the electromagnetic repulsive force that will immobilize the bone migration site similar to a magnetic levitation train.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and devices disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
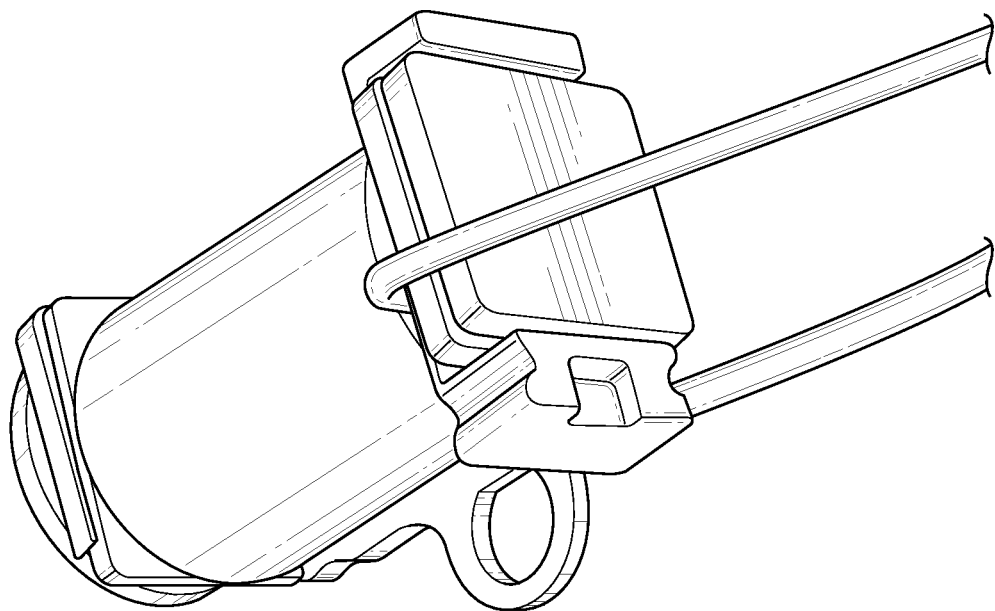
FIG. 1 is a diagram depicting a micro-electromagnet according to exemplary embodiments of the present technology.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

In various embodiments the present technology substitutes pins, rods, and external casts with micro-electromagnets secured to bone structure (i.e., using bone meal, epoxy, and/or bone scoring). In some embodiments equipment similar to that which is used for pacemakers is used with the present technology. For example, external equipment may resemble equipment used for a diabetic insulin pump. For instance, a power supply (e.g., long draw pacemaker batteries approved for use inside the human body) could remain external to the body of a patient (i.e., resemble the insulin pump) with a pigtail of positive and negative leads going into the body of the patient. The positive and negative electromagnets may be connected using bone meal and epoxy to the healthy bone structure at an appropriate angle to immobilize the fracture site when current is supplied resulting in magnetic attraction. Furthermore, amperage may be increased or decreased in various embodiments as necessary to provide additional pressure if the injury site is likely to have movement of the muscular tissue around the injury site in order to immobilize the fracture site.

In various embodiments of the present technology amperage can be decreased by medical practitioners incrementally as healing occurs for a patient. For example, medical practitioners may use Bluetooth technology to communicate with a power supply. In contrast, inserting hardware (i.e., "all or nothing" pins, rods, casts, and other hardware) may not be dynamically adjusted. In some instances, micro-electromagnets used with the present technology may be left in place (e.g., in the body of a patient on the bone structure)

with positive and negative leads being removed laparoscopically to allow for continual hyper localization of the injury site.

In various embodiments of the present technology after insertion of the electromagnets, the surgical site may be sewn up so that only one main electrode pigtail leads out from the body minimizing the risk of infection and decreasing tissue healing time for a patient. In contrast, insertion of currently available hardware (e.g., protruding rods, fixators, etc.) may be more likely to cause infection of the injury site for the patient.

FIG. 1 is a diagram depicting a micro-electromagnet 100 according to exemplary embodiments of the present technology. The diagram depicts a micro-electromagnet 100 shown as a square shape and a positive lead connected to the power supply (not shown). For example, in various embodiments the first micro-electromagnet placed in the first bracket and secured to the first side of the fractured bone of the bone fracture injury site is square shaped; and the second micro-electromagnet placed in the second bracket and secured to the second side of the fractured bone of the bone fracture injury site is also square shaped.

Figure 2:
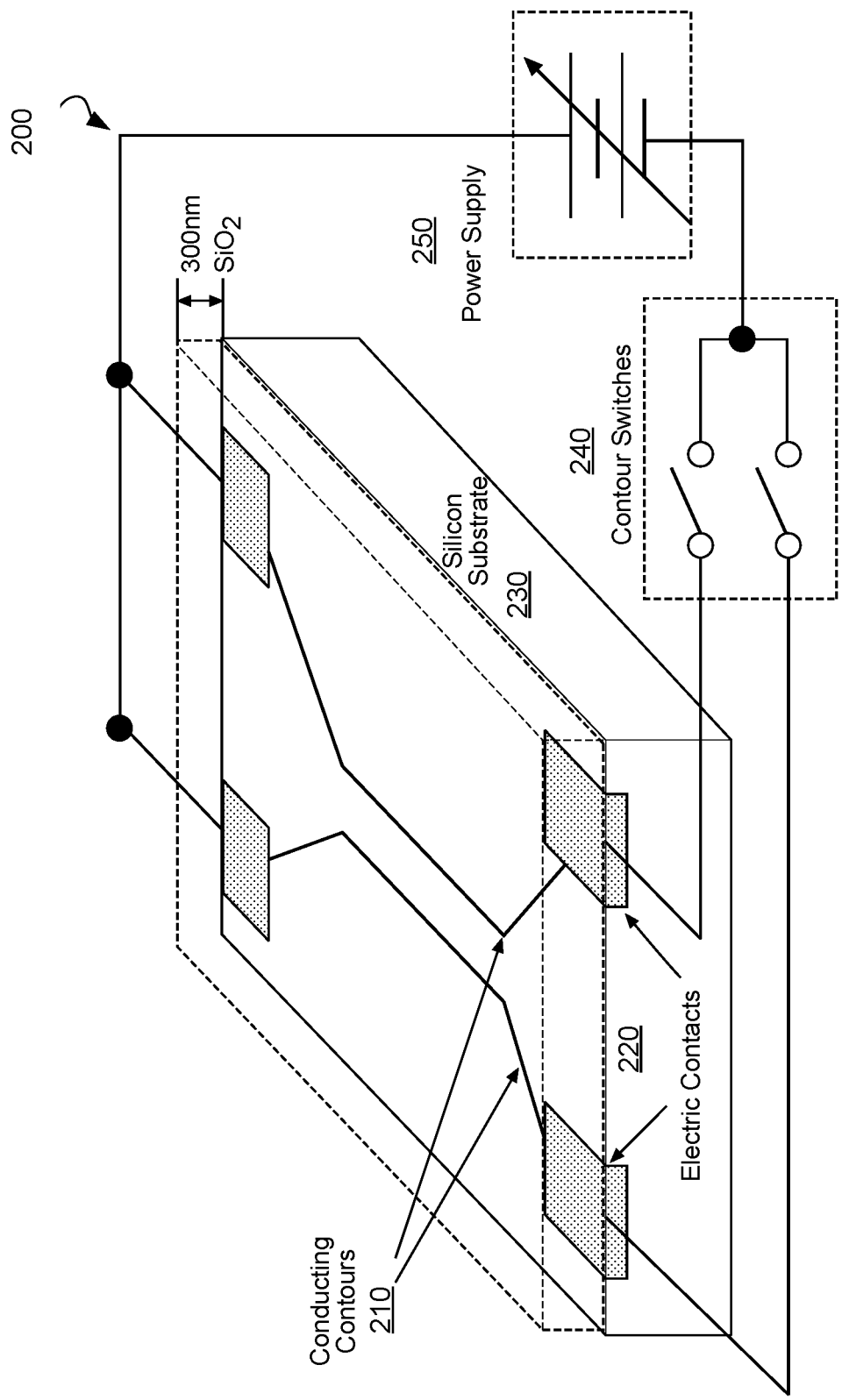
FIG. 2 is a close-up schematic diagram depicting a micro-electromagnet according to exemplary embodiments of the present technology.

FIG. 2 is a close-up schematic diagram depicting a micro-electromagnet 200 according to exemplary embodiments of the present technology. The close-up schematic diagram depicting a micro-electromagnet 200 shows conducting contours 210, electric contacts 220, a silicon substrate 230, contour switches 240, and a power supply 250. In various embodiments the power supply being external to the patient provides increased electric current compared with a baseline of the electric current, the increased electric current causing increased pressure of the bone fracture injury site compared with a baseline pressure that enhances immobilization of the fractured bone of the bone fracture injury site allowing for personalized healing of the bone fracture injury site. For example, the contour switches 240 may be used to increase the electric current from the power supply 250 to the electric contacts 220. In some embodiments the power supply provides decreased electric current compared with a baseline of the electric current, the decreased electric current causing decreased pressure of the bone fracture injury site compared with a baseline pressure that diminishes immobilization of the fractured bone of the bone fracture injury site allowing for personalized healing of the bone fracture injury site. For example, the contour switches 240 may be used to decrease the electric current from the power supply 250 to the electric contacts 220.

In various embodiments the present technology enables a medical practitioner to incrementally decrease the electromagnetic pressure as a patient progress through healing. Thus, adjusting the pressure allows for personalized patient physical therapy and healing. In contrast, hardware solutions are an all or nothing solution for immobilization because your either have the hardware installed or you do not. The present technology allows a medical practitioner to change the pressure by changing the current from the power source to a patient can have personalized healing. For example, if a patient is transitioning from bed rest to beginning to stand and then progressing towards walking the medical practitioner may vary the pressure—likely increasing the pressure and immobilization as new movements are attempted and the body is placed under different loading, and then decreasing the pressure incrementally to test the patient's healing and determine the strength of the bonded bone.

Figure 3:
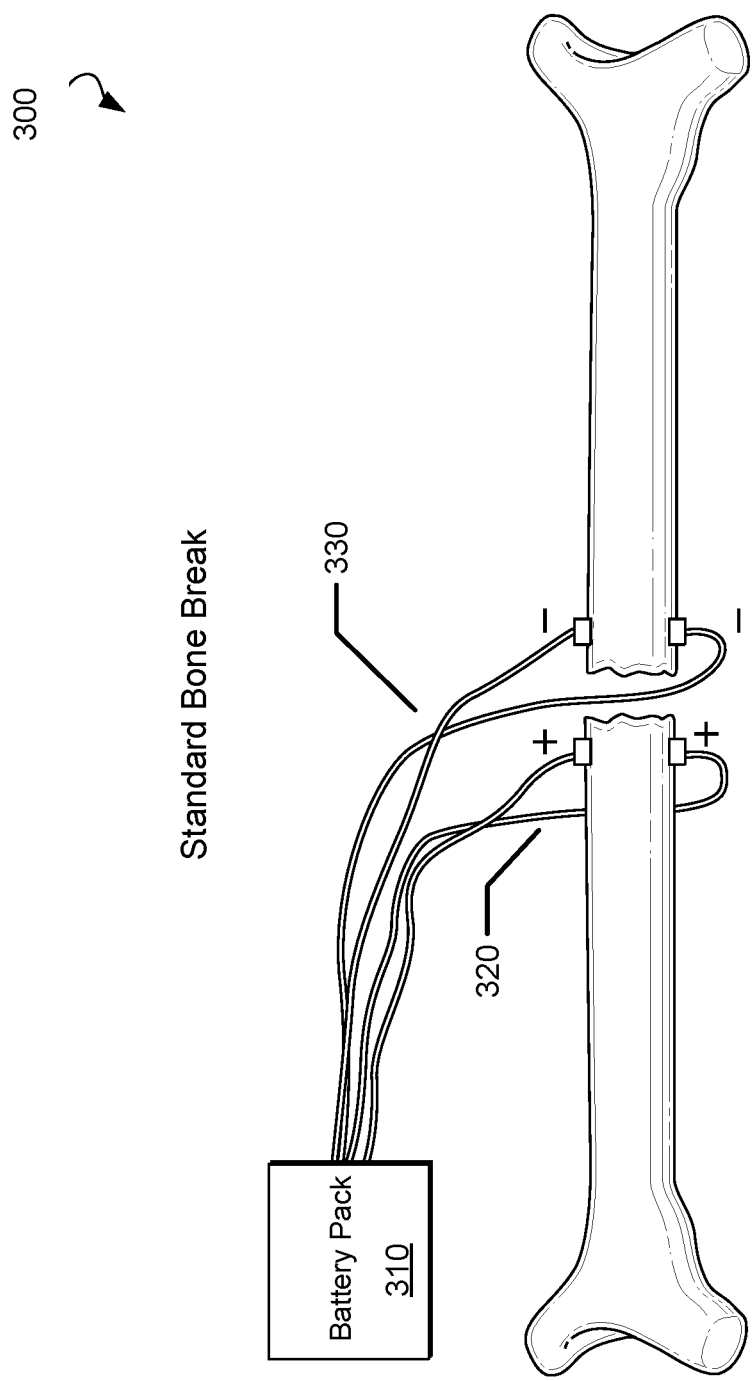
FIG. 3 is a diagram depicting micro-electromagnets connected to a battery pack and attached to both sides of a standard bone fracture for hyper-localized immobilization and healing of the standard bone fracture according to exemplary embodiments of the present technology.
Figure 4:
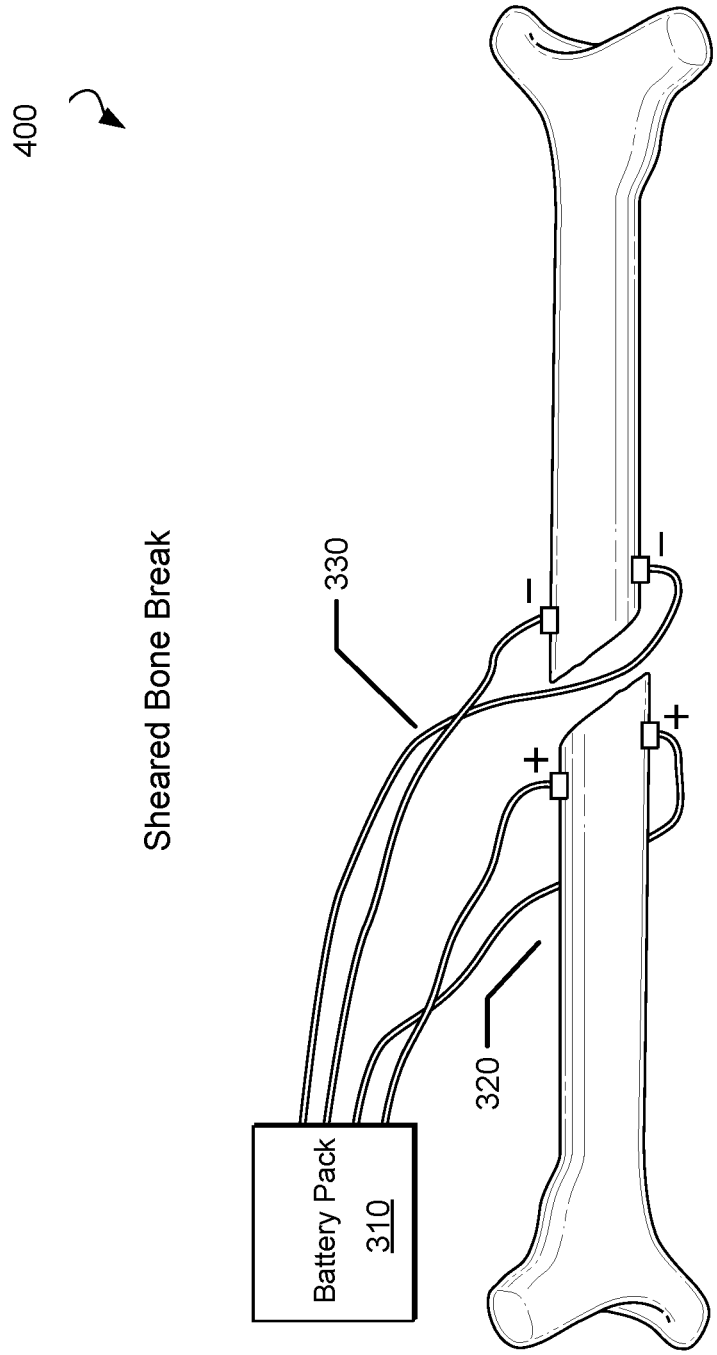
FIG. 4 is a diagram depicting micro-electromagnets connected to a battery pack and attached to both sides of a sheared bone fracture for hyper-localized immobilization and healing of the sheared bone fracture according to exemplary embodiments of the present technology.

FIG. 3 and FIG. 4, show systems for hyper-localized immobilization of a bone fracture injury site using micro-electromagnets placed in brackets that are secured to fractured bone of the bone fracture injury site causing accelerated healing. FIG. 3 and FIG. 4, show systems comprising: a power supply (e.g., a battery pack), the power supply being external to a patient and allowing control of electric current from the power supply; a first micro-electromagnet being internal to the patient and placed in a first bracket that is secured to a first side of the fractured bone of the bone fracture injury site, the first micro-electromagnet being electronically connected to a positive lead connected to the power supply, the positive lead receiving the electric current from the power supply causing half of an electromagnetic attractive force that will immobilize the fractured bone of the bone fracture injury site; and a second micro-electromagnet being internal to the patient and being placed in a second bracket secured to a second side of the fractured bone of the bone fracture injury site, the second micro-electromagnet being electrically connected to a negative lead connected to the power supply, the negative lead receiving the electric current from the power supply causing the other half of an electromagnetic attractive force that will immobilize the fractured bone of the bone fracture injury site.

FIG. 3 is a diagram depicting micro-electromagnets connected to a battery pack and placed in brackets that are attached to both sides of a standard bone fracture 300 for hyper-localized immobilization and healing of the standard bone fracture according to exemplary embodiments of the present technology. The diagram depicts micro-electromagnets connected to a battery pack (i.e., battery pack 310) and placed in brackets that are attached to both sides of a standard bone fracture 300 includes the battery pack 310 and a positive lead 320 connected to the power supply, the positive lead receiving the electric current from the power supply causing half of an electromagnetic attractive force that will immobilize the fractured bone (e.g., standard bone fracture) of the bone fracture injury site and a negative lead 330 connected to the power supply, the negative lead receiving the electric current from the power supply causing the other half of an electromagnetic attractive force that will immobilize the fractured bone (e.g., standard bone fracture) of the bone fracture injury site.

FIG. 4 is a diagram depicting micro-electromagnets connected to a battery pack and placed in brackets that are attached to both sides of a sheared bone fracture 400 for hyper-localized immobilization and healing of the sheared bone fracture according to exemplary embodiments of the present technology. The diagram depicts micro-electromagnets connected to a battery pack (i.e., battery pack 310) and placed in brackets that are attached to both sides of a sheared bone fracture 400 includes the battery pack 310 and a positive lead 320 connected to the power supply, the positive lead receiving the electric current from the power supply causing half of an electromagnetic attractive force that will immobilize the fractured bone (e.g., sheared bone fracture) of the bone fracture injury site and a negative lead 330 connected to the power supply, the negative lead receiving the electric current from the power supply causing the other half of an electromagnetic attractive force that will immobilize the fractured bone (e.g., sheared bone fracture) of the bone fracture injury site.

Figure 5:
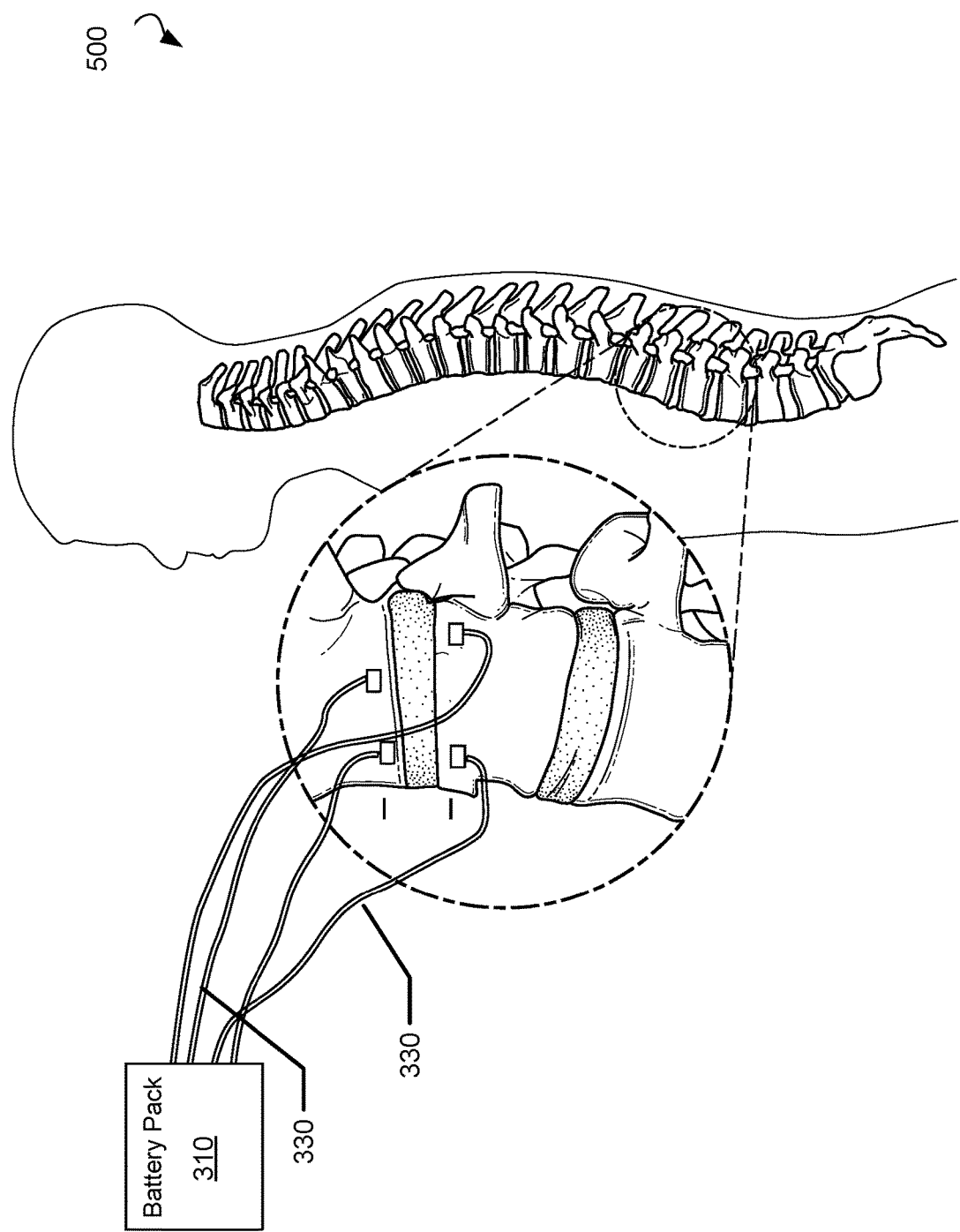
FIG. 5 is a diagram depicting micro-electromagnets connected to a battery pack and attached to vertebrae on opposite sides of a compressed vertebral disc in the lumbar spine to facilitate hyper-localized precise repulsive force. immobilization/stabilization/fixation according to exemplary embodiments of the present technology.

FIG. 5 is a diagram depicting micro-electromagnets connected to a battery pack and placed in brackets that are attached to the vertebrae above and the vertebrae below a compressed vertebral disc in the lumbar spine 500 to facilitate hyper-localized precise repulsive force immobilization/stabilization/fixation according to exemplary embodiments of the present technology.

The diagram of FIG. 5 depicts micro-electromagnets connected to a battery pack (i.e., battery pack 310) and attached to both sides of a compromised vertebral disc in the lumbar spine 500 and includes the battery pack 310 and two sets of negative leads 330 connected to the power supply, both negative leads receiving the electric current from the power supply generating an electromagnetic repulsive force that prevents encroachment or migration of bone structures (e.g. vertebrae in the lumbar spine) beyond prescribed parameters (e.g. the thickness of healthy, non-compressed vertebral discs).

In various embodiments the diagram of FIG. 3, FIG. 4, and FIG. 5 may each have the electromagnet's electrical leads braided or pigtailed such that they exit the patient from fewer wound sites instead of having multiple entrances or wound cavities that are present when using rods and other hardware. Using a pigtail for the leads decreases that a chance for infection because there are fewer entrance points to the patient and the electrical leads and pigtail removed by a laparoscopic or other "minimally invasive" procedure following the pigtail's tunnel through the healed surrounding tissue which would in turn be less traumatic for the patient.

In various embodiments the micro-electromagnets placed in brackets as shown is FIG. 3, FIG. 4, and FIG. 5 are secured to the bone structure using epoxy and bone meal and the like. In some embodiments bone scoring may be used to enhance healing. In some embodiments the brackets are secured to the fractured bone using dental resin that is cured using ultraviolet light. For example, the first bracket is secured to the first side of the fractured bone of the bone fracture injury site using epoxy and bone meal; and the second bracket is secured to the second side of the fractured bone of the bone fracture injury site using epoxy and bone meal. In various embodiments the first bracket in which the first micro-electromagnet is placed is secured to the first side of the fractured bone of the bone fracture injury site using dental resin cured using ultraviolet light; and the second bracket in which the second micro-electromagnet is placed is secured to the second side of the fractured bone of the bone fracture injury site using dental resin cured using ultraviolet light.

The terminology used herein is for the purpose of describing particular embodiments only and is not intended to be limiting of the technology. As used herein, the singular forms "a", "an" and the are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity. While this technology is susceptible of embodiments in many different forms, there is shown in the drawings and has been described in detail several specific embodiments with the understanding that the present disclosure is to be considered as an exemplification of the principles of the technology and is not intended to limit the technology to the embodiments illustrated.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three-dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below", or "beneath" other elements would then be oriented "above" the other elements. Therefore, the example terms "below" and "lower" can, therefore, encompass both an orientation of above and below.

The description of the present disclosure has been presented for purposes of illustration and description but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

While various embodiments have been described above, it should be understood that they have been presented by way of example only, and not limitation. The descriptions are not intended to limit the scope of the technology to the forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A system for hyper-localized immobilization, stabilization, and/or fixation of bone structures using micro-electromagnets secured to surrounding bone structures of a bone fracture injury site causing accelerated healing for a patient, the system comprising:
    a power supply, the power supply generating variable electric current supplied to micro-electromagnets connected to the power supply;
    a first micro-electromagnet being internal to the patient and being placed within a first bracket that is configured to be secured to a first side of the surrounding bone structures of the bone fracture injury site, the first micro-electromagnet being electronically connected to a positive lead connected to the power supply, the positive lead receiving the variable electric current from the power supply causing a first half of an electromagnetic attractive force that immobilizes the bone fracture injury site and a first part of an electromagnetic repulsive force that creates bone spacing; and
    a second micro-electromagnet being internal to the patient and being placed within a second bracket that is secured to a second side of the surrounding bone structures of the bone fracture injury site, the second micro-electromagnet being electrically connected to a negative lead connected to the power supply, the
    negative lead receiving the variable electric current from the power supply causing a second half of the electromagnetic attractive force that immobilizes the bone fracture injury site and a second part of the electromagnetic repulsive force that creates bone spacing.

2. The system of claim 1,
    wherein the first bracket is configured to be secured to the first side of the surrounding bone structures of the bone fracture injury site using epoxy and bone meal; and
    wherein the second bracket is configured to be secured to the second side of the surrounding bone structures of the bone fracture injury site using epoxy and bone meal.

3. The system of claim 2,
    wherein the first side of the surrounding bone structures of the bone fracture injury site is mechanically scored for enhanced healing of the bone fracture injury site and to create a male coupling joint; and
    wherein the second side of the surrounding bone structures of the bone fracture injury site is mechanically scored for enhanced healing of the bone fracture injury site and to create a female coupling joint.

4. The system of claim 1,
    wherein the first bracket is configured to be secured to the first side of the surrounding bone structures of the bone fracture injury site using dental resin cured using ultraviolet light; and
    wherein the second bracket is configured to be secured to the second side of the surrounding bone structures of the bone fracture injury site using dental resin cured using ultraviolet light.

5. The system of claim 1, wherein the power supply provides increased electric current relative to a baseline of electric current, the increased electric current causing increased pressure at the bone fracture injury site relative to a baseline pressure that enhances immobilization of fractured bone of the bone fracture injury site allowing for personalized healing of the bone fracture injury site.

6. The system of claim 1, wherein the power supply provides decreased electric current relative to a baseline of electric current, the decreased electric current causing decreased pressure at the bone fracture injury site relative to a baseline pressure that diminishes immobilization of fractured bone of the bone fracture injury site allowing for personalized healing of the bone fracture injury site.

7. The system of claim 1,
    wherein the first micro-electromagnet placed within the first bracket that is configured to be secured to the first side of the surrounding bone structures of the bone fracture injury site is square shaped; and
    wherein the second micro-electromagnet placed within the second bracket that is configured to be secured to the second side of the surrounding bone structures of the bone fracture injury site is square shaped.

8. The system of claim 1,
wherein fractured bone of the bone fracture injury site is treated with stems cells to enhance healing of the bone fracture injury site.

9. The system of claim 1, further comprising:
a first plurality of micro-electromagnets being internal to the patient and being configured to be secured to the first side of the surrounding bone structures of the bone fracture injury site, the first plurality of micro-electromagnets enhancing electromagnetic fields of the first micro-electromagnet; and
a second plurality of micro-electromagnets being internal to the patient and being configured to be secured to the second side of the surrounding bone structures of the bone fracture injury site, the second plurality of micro-electromagnets enhancing electromagnetic fields of the second micro-electromagnet.

10. A method for hyper-localized immobilization, stabilization, and/or fixation of bone structures using micro-electromagnets configured to be secured to surrounding bone structures of a bone fracture injury site causing accelerated healing for a patient, the method comprising:
generating variable electric current, using a power supply, the variable electric current being supplied to micro-electromagnets connected to the power supply;
receiving the variable electric current at a first micro-electromagnet that is internal to the patient and placed within a first bracket that is configured to be secured to a first side of the surrounding bone structures of the bone fracture injury site, the first micro-electromagnet being electronically connected to a positive lead connected to the power supply, the positive lead receiving the variable electric current from the power supply causing a first half of an electromagnetic attractive force that immobilizes the bone fracture injury site and a first part of an electromagnetic repulsive force that creates bone spacing; and
receiving the variable electric current at a second micro-electromagnet that is internal to the patient and is placed within a second bracket that is configured to be secured to a second side of the surrounding bone structures of the bone fracture injury site, the second micro-electromagnet being electrically connected to a negative lead connected to the power supply, the negative lead receiving the variable electric current from the power supply causing a second half of the electromagnetic attractive force that immobilizes the bone fracture injury site and a second part of the electromagnetic repulsive force that creates bone spacing.

11. The method of claim 10,
wherein the first bracket is configured to be secured to the first side of the surrounding bone structures of the bone fracture injury site using epoxy and bone meal; and
wherein the second bracket is configured to be secured to the second side of the surrounding bone structures of the bone fracture injury site using epoxy and bone meal.

12. The method of claim 11,
wherein the first side of the surrounding bone structures of the bone fracture injury site is mechanically scored for enhanced healing of the bone fracture injury site and to create a male coupling joint; and
wherein the second side of the surrounding bone structures of the bone fracture injury site is mechanically scored for enhanced healing of the bone fracture injury site and to create a female coupling joint.

13. The method of claim 10, wherein the first bracket is configured to be secured to the first side of the surrounding bone structures of the bone fracture injury site using dental resin cured using ultraviolet light; and
wherein the second bracket is configured to be secured to the second side of the surrounding bone structures of the bone fracture injury site using dental resin cured using ultraviolet light.

14. The method of claim 10, further comprising:
generating, using the power supply, increased electric current relative to a baseline of electric current, the increased electric current causing increased pressure at the bone fracture injury site relative to a baseline pressure that enhances immobilization of fractured bone of the bone fracture injury site allowing for personalized healing of the bone fracture injury site.

15. The method of claim 10, further comprising:
generating, using the power supply, decreased electric current relative to a baseline of electric current, the decreased electric current causing decreased pressure at the bone fracture injury site relative to a baseline pressure that diminishes immobilization of fractured bone of the bone fracture injury site allowing for personalized healing of the bone fracture injury site.

16. The method of claim 10,
wherein the first micro-electromagnet placed within the first bracket that is configured to be secured to the first side of the surrounding bone structures of the bone fracture injury site is square shaped; and
wherein the second micro-electromagnet placed within the second bracket that is configured to be secured to the second side of the surrounding bone structures of the bone fracture injury site is square shaped.

17. The method of claim 10,
wherein fractured bone of the bone fracture injury site is treated with stems cells to enhance healing of the bone fracture injury site.

18. A method for hyper-localized immobilization, stabilization, and/or fixation of bone structures using micro-electromagnets configured to be secured to surrounding bone structures of a bone fracture injury site causing accelerated healing for a patient, the method comprising:
generating variable electric current, using a power supply, the variable electric current being supplied to micro-electromagnets connected to the power supply;
receiving the variable electric current at a first micro-electromagnet that is internal to the patient and placed within a first bracket that is configured to be secured to a first side of the surrounding bone structures of the bone fracture injury site, the first micro-electromagnet being electronically connected to a positive lead connected to the power supply, the positive lead receiving the variable electric current from the power supply causing a first half of an electromagnetic attractive force that immobilizes the bone fracture injury site and a first part of an electromagnetic repulsive force that creates bone spacing;
receiving the variable electric current at a second micro-electromagnet that is internal to the patient and is placed within a second bracket that is configured to be secured to a second side of the surrounding bone structures of the bone fracture injury site, the second micro-electromagnet being electrically connected to a negative lead connected to the power supply, the negative lead receiving the variable electric current from the power supply causing a second half of the electromagnetic attractive force that immobilizes the bone fracture injury site and a second part of the electromagnetic repulsive force that creates bone spacing; and generating, using the power supply, increased electric current relative to a baseline of electric current, the increased electric current causing increased pressure at the bone fracture injury site relative to a baseline pressure that enhances immobilization of fractured bone of the bone fracture injury site allowing for personalized healing of the bone fracture injury site.

19. The method of claim 18, further comprising:

generating, using the power supply, decreased electric current relative to a baseline of electric current, the decreased electric current causing decreased pressure at the bone fracture injury site relative to a baseline pressure that diminishes immobilization of fractured bone of the bone fracture injury site allowing for personalized healing of the bone fracture injury site.

20. The method of claim 19, further comprising treating the patient with stem cell therapy to promote accelerated healing of fractured bone of the bone fracture injury site.

* * * * *